United States Patent [19]

Rainsford et al.

[11] Patent Number: 4,885,279

[45] Date of Patent: Dec. 5, 1989

[54] PHARMACEUTICAL FORMULATION CONTAINING INDOMETHACIN

[76] Inventors: Kim D. Rainsford, No. 1 Butt Lane, Great Wilbraham, Cambridgeshire, England; Michael W. Whitehouse, 43 Malcolm Street, Millswood, South Australia

[21] Appl. No.: 30,563

[22] Filed: Mar. 27, 1987

[30] Foreign Application Priority Data

Mar. 27, 1986 [GB] United Kingdom .............. 8607662

[51] Int. Cl.$^4$ ................... A61K 31/53; A61K 31/70
[52] U.S. Cl. ................................. 514/23; 514/415; 514/777
[58] Field of Search .................... 514/23, 777, 415

[56] References Cited

U.S. PATENT DOCUMENTS 4,440,762  4/1984  Rainsford et al. ............. 514/161

FOREIGN PATENT DOCUMENTS 0013783  8/1980  European Pat. Off. .
0154523  9/1985  European Pat. Off. .

OTHER PUBLICATIONS

Rainsford, "The Comparative Gastric Ulcerogenic Activities of Non-Steroid Anti-Inflammatory Drugs", *Agents and Actions,* 7:573-7 (1977).

*Primary Examiner*—Ronald W. Griffin
*Attorney, Agent, or Firm*—Banner, Birch, McKie & Beckett

[57] ABSTRACT

A pharmaceutical preparation comprising indomethacin as active anti-inflammatory drug and a metabolizable carbohydrate and a salt of a metabolic carboxylic acid and a metabolizable carbohydrate to protect both the stomach and the intestinal tract against damage by the drug.

13 Claims, No Drawings

PHARMACEUTICAL FORMULATION CONTAINING INDOMETHACIN

The invention relates to a pharmaceutical formulation containing the drug indomethacin. This formulation, when taken orally, prevents damage comprising ulceration, mucosal lesions, bleeding and peritonitis, to both the stomach as well as the lower regions of the small and large intestine.

Certain anti-inflammatory drugs, in particular aspirin, are known to cause gastric damage, i.e. to the stomach, but no appreciable damage to the large or small intestine. In contrast, damage can be caused to the intestinal tract by indomethacin as well as that in the stomach. The former can be very severe and relatively high doses of the drug administered over a period of a few days have induced fatal peritonitis in laboratory rats. In rare instances, such fatal intestinal peritonitis as well as ulceration in the stomach have occurred in human patients treated with indomethacin.

Although the damage to both the gastric mucosa and lower intestinal tract appears partly related to the activity of indomethacin as a potent inhibitor of prostaglandin synthesis, it is important to recognise that the mechanisms of gastric damage and damage to the lower portions of the intestinal tract are in fact quite different. The prostaglandins normally synthesised by certain cells on the surface of the gastrointestinal mucosa protect this tissue from the action of the many irritating agents. Blockage of the synthesis of these natural protectants therefore exposes the mucosa of the gastrointestinal tract to other actions of these anti-inflammatory drugs, e.g. surface mucosal irritation, energy depletion, oxyradical-induced cell injury etc. Thus antigens normally present in the intestine, many of which are derived from the coliform bacteria that are normally present therein, enhance the damage in this region produced by indomethacin. Tests have shown that if no bacteria are present, indomethacin does not cause intestinal damage. It is also known that the unusual metabolism and pharmacokinetics of indomethacin which are responsible for the recycling of this drug from the bile to be absorbed back through the intestinal mucosa are a major feature accounting for damage in the latter region.

It has been previously shown that a mixture of a metabolisable carbohydrate and an alkali metal or alkaline earth metal salt of a carboxylic acid acts as a gastric protectant when administered in conjunction with certain anti-inflammatory drugs that are known to cause damage to the stomach such as aspirin and azapropazone.

We have now surprisingly discovered that, in spite of the great differences between the intrinsic functioning of the environment (e.g. pH, presence of proteolytic and other enzymes) in the stomach compared with the intestine, such a protective mixture will protect not only the gastric but also the intestinal tract against damage by the drug indomethacin, provided that the ratio of at least one, and preferably both, of the components of the protective mixture to the drug is very substantially increased over the optimum ratio for gastric protection found previously with aspirin or azapropazone.

Thus according to this invention there is provided a pharmaceutical formulation comprising indomethacin or a salt thereof, a pharmaceutically-acceptable metabolisable carbohydrate, and an alkali metal, alkaline earth metal, or ammonium salt of a metabolic carboxylic acid, the weight ratios of both indomethacin:carbohydrate and indomethacin:carboxylic acid salt being in the range 1:3 to 1:20, provided that at least one of said weight ratios is within the range of 1:10 to 1:20.

Preferably the weight ratio indomethacin:carbohydrate:carboxylic acid salt is within the range 1:3:10 to 1:10:3, and more preferably 1:3:15 to 1:15:3 to 1:3:20 to 1:20:3. It may be preferable for the indomethacin:carboxylic acid salt weight ratio to be the same as the indomethacin:carbohydrate ratio, in which case the ratio indomethacin; carboxylic acid salt:carbohydrate weight ratio may be 1:10:10 or more preferably 1:15:15 or 1:20:20.

Preferred carboxylates are citrate or succinate, and the preferred carbohydrate is D-glucose except for administration to diabetics where fructose would be a more suitable alternative. Other alternatives are galactose, mannose, arabinose, ribose, lactose and N-acetyl-glucosamine. By a "metabolic carboxylic acid" is meant one of the acids which are necessary to the efficient metabolism of intermediates resulting from the oxidative metabolism of glucose eventually to form ATP, that is those intermediates or precursors of the tricarboxylate (Krebs) metabolic cycle. Other examples of such salts are succinate and oxaloacetates. Precursors of such acids can also be used: for example glutamate and aspartate are precursors of α-ketoglutarate and oxaloacetate respectively.

The salt is preferably a sodium salt and may be an acid salt such as sodium dihydrogen citrate or disodium hydrogen citrate.

The formulation is preferably prepared by blending together the ingredients, optionally including an excipient, at a temperature below 30° C. In the case of an aqueous formulation, the pH is controlled so that it remains below 8. Dry formulations may be filled into capsules for oral adminstration.

Indomethacin has the following chemical formula:

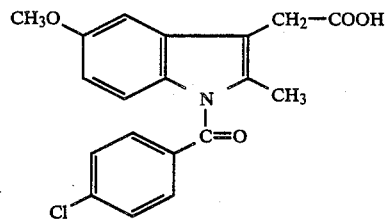

More than one metabolisable carbohydrate and metabolic carboxylate salt may be included in the formulation if desired. Further, pharmaceutically-acceptable excipients may be added if desired. The formulation may be prepared in solid or liquid (including dispersed) form, and, as will be demonstrated, significantly reduces the number and/or the severity of the mucosal lesions or ulcers occurring in both the stomach wall as well as the intestinal tract as compared with the same dosage of the drugs alone.

Advantages of the present invention will become clearer from a consideration of the following examples:

EXAMPLE 1

Male Sprague Dawley rats in whom arthritis has been induced by prior innoculation with heat killed *Mycobacterium tuberculosis*, were dosed orally for 4 days in the morning and evening (at approximately 10 hour time difference) with divided doses of 10 mg/kg/d indomethacin as either (a) the pure drug suspension alone, or (b) in the weight ratios shown in the table of added disodium hydrogen citrate and D-glucose monohydrate (both of British Pharmacopeal grade); the ratios indicated are with respect to indomethacin given=1. On the evening of the last day of dosage the animals were fasted and the next morning they were killed (i.e. the period of the experiment lasted 5 days), for the determination of ulcers in the stomach (gastric mucosa) and intestinal tract. Where ulcers were present in the intestinal tract they in all cases gave rise to peritonitis so the recording of such damage is given as percent animals with peritonitis. N-7 for group. An excipient DC350 was added to all indomethacin formulations to lubricate the powder since this was also added in the capsule materials used in the studies performed in human volunteers (shown in Example 2).

The addition of the excipient in no way affects the stability tests which have shown that the formulations of the present invention remain stable under normal storage conditions for at least six months.

TABLE
EFFECTS OF REPEATED DAILY ADMINISTRATIONS OF INDOMETHACIN FORMULATIONS ON THE GASTRO-INTESTINAL TRACT OF ARTHRITIC RATS

| DRUG TREATMENT | Animals with gastric lesions | No. of Gastric lesions (mean #SE) | Percent Animals with Intestinal Peritonitis |
| --- | --- | --- | --- |
| (a) INDOMETHACIN alone 10 mg/kg/d | 86% | 7.8 ± 5.5 | 86% |
| (b) INDOMETHACIN FORM. | | | |
| 1:10:10 (by weight) | 0 | 0 | 0 |
| 1:15:15 (by weight) | 0 | 0 | 0 |
| 1:20:20 (by weight) | 0 | 0 | 0 |
| CONTROL 1 ml H$_2$O/d | 0 | 0 | 0 |

Results consistent with the above use confirmed by scanning electron microscopy on the surface stomach mucosa of mice. That procedure allows for surface microscopic changes to be observed.

EXAMPLE 2

Chromium-51 blood loss studies were carried out on human volunteers, using indomethacin alone, and indomethacin/D-glucose/sodium dihydrogen citrate in weight proportions, of 1:3:3 and 1:10:10, 1:15:15 and 1:20:20 respectively. Chromium-51 is a radioisotope that can be used to label red blood cells and the presence of which in the faeces can be detected quantitatively to provide a measure of the combined blood losses from the stomach and the small and large intestine. The results of these tests indicated that whilst no improvement over indomethacin alone was detected with the 1:3:3 formulation, administration of the 1:10:10, 1:15:15 and 1:20:20 formulations was followed by a statistically-significant reduction in total blood less.

EXAMPLE 3

Studies were carried out in another model of gastric ulceration, details of which have been published previously (Rainsford K. D. 1975 Agents and Actions, vol. 5, p. 552) in which rats are given single doses of indomethacin orally at a dosage level of 30 mg/kg or indomethacin at the same dosage level with D-glucose and sodium dihydrogen citrate in the weight proportions indomethacin:D-glucose:sodium dihydrogen citrate of 1:15:15, or 1:3:15 or 1:15:3. The rats were subjected to a period of cold stress at 4° C. for a total of 3 hours after being dosed, and then they were killed, and the number of gastric lesions determined. All of the compositions containing glucose and citrate resulted in a much lower incidence of lesion formation than indomethacin alone, although the 1:15:15 formulation gave slightly better results than either the 1:3:15 or the 1:15:3 formulation.

We claim:

1. A pharmaceutical formulation comprising indomethacin or a salt thereof, a pharmaceutically-acceptable metabolisable carbohydrate, and an alkali metal, alkaline earth metal, or ammonium salt of a metabolic carboxylic acid, the weight ratios of both indomethacin:carbohydrate and indomethacin:carboxylic acid salt being in the range of 1:3 to 1:20, provided that at least one of said weight ratios is within the range 1:10 to 1:20.

2. A pharmaceutical formulation according to claim 1, wherein the weight ratio indomethacin:carbohydrate:carboxylic acid salt is within the range 1:3:15 to 1:15:3.

3. A pharmaceutical formulation according to claim 2, wherein the said weight ratio is within the range 1:3:10 to 1:10:3.

4. A pharmaceutical formulation according to claim 3, wherein the weight ratios indomethacin:carbohydrate and indomethacin:carboxylic acid salt are the same.

5. A pharmaceutical formulation according to claim 4 wherein the weight ratio indomethacin:carbohydrate:carboxylic acid salt is from 1:10:10 to 1:20:20.

6. A pharmaceutical formulation according to claim 5, wherein the said weight ratio is 1:15:15.

7. A pharmaceutical formulation according to any preceding claim wherein the metabolisable carbohydrate is D-glucose or fructose.

8. A pharmaceutical formulation according to claim 7 wherein the metabolic carboxylic acid is a citrate or a succinate.

9. A pharmaceutical formulation according to claim 7, including one or more pharmaceutically-acceptable excipients.

10. A pharmaceutical formulation according to claim 1, comprising indomethacin, D-glucose, and sodium dihydrogen citrate and/or dissodium hydrogen citrate, in a weight ratio within the range 1:15:15 to 1:20:20.

11. A process for the preparation of a pharmaceutical formulation comprising blending together at a temperature below 30° C., optionally with an excipient, indomethacin or a salt thereof, a pharmaceutically-acceptable metabolisable carbohydrate, and an alkali metal, alkaline earth metal, or ammonium salt of a metabolic carboxylic acid, the weight ratios of both indomethacin:carbohydrate and indomethacin:carboxylic acid salt being in the range of 1:3 to 1:20, provided that at least one of said weight ratios is within the range of 1:10 to 1:20.

12. A process according to claim 11 wherein the ingredients are blended together in the presence of water, and the pH is controlled so that it remains below 8.

13. A process according to claim 11, including the step of filing the formulation into capsules to obtain a product for oral administration.

* * * * *